United States Patent [19]
Birnbaum

[11] Patent Number: 5,456,262
[45] Date of Patent: Oct. 10, 1995

[54] METHOD FOR CALCULATING A FITNESS INDEX

[75] Inventor: Burton H. Birnbaum, Woodmere, N.Y.

[73] Assignee: Polar Electro Oy, Kempele, Finland

[21] Appl. No.: 144,018

[22] Filed: Nov. 1, 1993

[51] Int. Cl.⁶ ..................................................... A61B 5/02
[52] U.S. Cl. ..................................................... 128/707
[58] Field of Search ........................... 128/707, 903, 128/690, 687, 689, 696, 701, 632, 635

[56] References Cited

U.S. PATENT DOCUMENTS

| | | | |
|---|---|---|---|
| 4,624,733 | 12/1986 | Säynäjkanqas | 128/687 |
| 5,007,430 | 4/1991 | Dardih | 128/707 |
| 5,067,710 | 11/1991 | Watterson et al. | 272/129 |

FOREIGN PATENT DOCUMENTS

| | | | |
|---|---|---|---|
| 0117330 | 9/1984 | European Pat. Off. | 128/707 |

*Primary Examiner*—William E. Kamm
*Assistant Examiner*—Marianne Parker
*Attorney, Agent, or Firm*—Finnegan, Henderson, Farabow, Garrett & Dunner

[57] ABSTRACT

A method and a device for measuring the heartbeat pulse of a person during physical performance on an exercise device. The invention includes processing of a signal carrying pulse data and indicating the pulse frequency to the user of the exercise device. Included are the steps of programming the exercise device to provide a sequence of exercise to the performer, detecting and transmitting during the exercise a heartbeat pulse signal with electrodes and a transmitter attached to the body of the performer, receiving the transmitted pulse signal with a receiver connected to the exercise device, processing the received pulse signal, and calculating a mean pulse value during the performance and presenting the value to the performer.

7 Claims, 1 Drawing Sheet

METHOD FOR CALCULATING A FITNESS INDEX

FIELD OF THE INVENTION

This invention relates to a method and an apparatus for wireless measurement of the heartbeat of a person during physical performance on an exercise device, such as a cycle ergometer or a treadmill, including processing a signal carrying the heartbeat data and indicating the heartbeat to the user of the exercise device.

BACKGROUND OF THE INVENTION

In various kinds of exercising and fitness training, it has become common to measure the heartbeat with various handheld measuring devices based on wired or telemetric wireless transmission between a separate transmitter attached to the body and a receiver worn on the wrist. Such a device is described in U.S. Pat. No. 4,625,733, for example.

On the other hand, it is known to combine the use of programmable exercise devices, such as cycle ergometers, with the use of pulse measuring devices, such as in U.S. Pat. No. 5,067,710.

One very significant index of an individual's level of fitness is her or his mean pulse value calculated on pulse values measured during a whole exercise performance. This kind of index is, however, not useful if the performance varies from one time to another, which it invariably does in sports, due to outer circumstances, such as weather, disturbance from other people, mistakes by the performer himself etc. Looking into this problem the other way, there has so far not been a reliably and easily calculated index for indicating a constant level of heart performance at each fitness test occasion; which means that a certain heart performance index is the target and the exercise is continued and/or varied in order to achieve this target index.

OBJECT OF THE INVENTION

The object of the present invention is to provide a method for measuring a fitness index, which is easy to measure and calculate, and which is an accurate indicator of a person's fitness developmets when repeated with any frequency or over any period of time.

It is also an object of the present invention to provide an easy and reliable way for a person to achieve exactly or nearly exactly a constant level of performance each time a fitness test according to the invention is made.

It is a further object of the present invention to combine a distinctly known device for measuring heartbeat with an exercise device, such as a cycle ergometer or a treadmill, in order to provide an apparatus for computing the fitness index according to the invention.

SUMMARY OF THE INVENTION

The method according to the invention comprises in its broadest aspect the steps of:
  programming an exercise device to provide a predetermined sequence of excercise to the performer during a predetermined time interval;
  detecting and transmitting during said time interval the user's heartbeat signal with electrodes and a transmitter attached to the body of the performer;
  receiving the transmitted heartbeat signals and processing them to represent a pulse measurement value in a receiver connected to the exercise device;
  calculating the mean pulse value during the whole of said time interval and presenting the value to the performer.

A mean pulse value that tends to decrease in e.g. weekly or monthly repeated measurements means an increased fitness level; an increasing value means a reduced fitness level, or that something is wrong with the training program of the person in question.

In the case that the performance of the user's body, i.e. the "heart performance" is intended to be kept at a constant level, the inventive method may be used to provide a certain mean pulse value as an index. When the index value is reached, the exercise may be interrupted.

The apparatus according to the invention essentially comprises the combination of an exercise device, a heartbeat detector and a pulse signal transmitter, a pulse signal receiver with processing means for calculating a mean pulse value during a predetermined time interval, and display means to present the calculated mean pulse value to the performer.

Obviously, a modern programmable cycle ergometer or treadmill provide the easiest implementation of the exercise device of the present invention. It is, however, possible to provide also other types of exercise devices, such as rowing machines, with the neccessary facilities to carry out the invention.

Other preferred embodiments of the invention are discussed in the detailed description and in the attached claims.

DETAILED DESCRIPTION OF THE INVENTION

Figure 1:
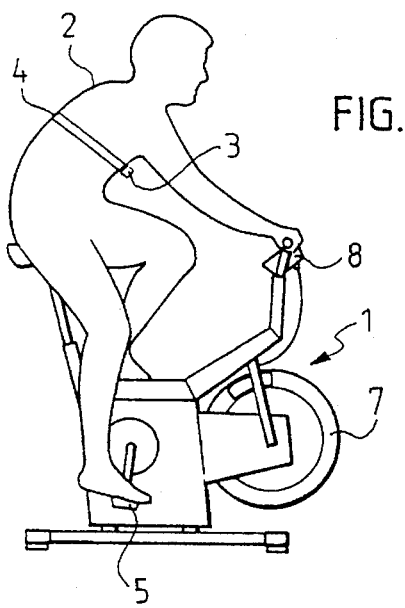
FIG. 1 is a general view of a modern cycle ergometer used by a person wearing a telemetric pulse transmitter on his body.

FIG. 1 shows a general view of a modern cycle ergometer 1 used by a person 2 wearing a telemetric pulse transmitter 3 attached with a strap 4 to the chest of his body. During exercise, the user is supposed to drive the pedals 5 at a steady pace during the test interval. The pedals engage through a chain 6 a back wheel 7, which is connected to a variable load or resistance device (not shown), controlled by a control unit 8 of the cycle ergometer.

The control unit 8 of the cycle ergometer 1 may be a microprocessor controlled timing and resistance controlling device, such as described in aforementioned U.S. Pat. No. 5,067,710. With the control unit, any exercise program including simulation of more or less steep hills and even runways following each other in desired sequences can be simulated. It is, briefly stated, possible to design any imaginable pattern of running resistance, within a desired test interval, for the cycle ergometer. The design of suitable test programs does not form part of this invention, and it is presumed that the person exercising has been provided by a suitable test program by his coach or physician.

During the exercise or the test period, the electrodes (not shown) attached to the chest of the user and forming part of the transmitter unit 3 means detect the heartbeat signal, which is converted in the transmitter into an ac signal supplying current to one or several telemetric coils in the transmitter unit 3. While passing through the coils, the ac signal generates a corresponding magnetic field, which is detected by a corresponding coil in the receiver means incorporated in or attached to the control unit 8. The basic technique of telemetric measurement is disclosed in aforementioned U.S. Pat. No. 4,625,733, the disclosure of which is incorporated here by reference. Obviously, it is possible within the context of the present invention to transmit and receive pulse signals by means of wired connections between the transmitter and receiver means.

Figure 2:
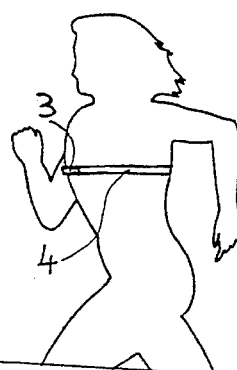
FIG. 2 is a general view of a modern treadmill used by a person wearing a telemetric pulse transmitter on his body.

In FIG. 2, a treadmill 6 is shown, which is used by a person wearing the telemetric pulse transmitter 3 attached with a strap 4 to the chest of his body. During exercise, the user is supposed to run on the running belt of the treadmill at a constant or variable pace during the test interval. The basic operation as well as the measuring and calculation principles of a fitness index are identical to the cycle ergometer case. As programmable treadmills are available on the market, it is likewise known to physicians or coaches how to design suitable test programs for persons exercising on a treadmill.

Figure 3:
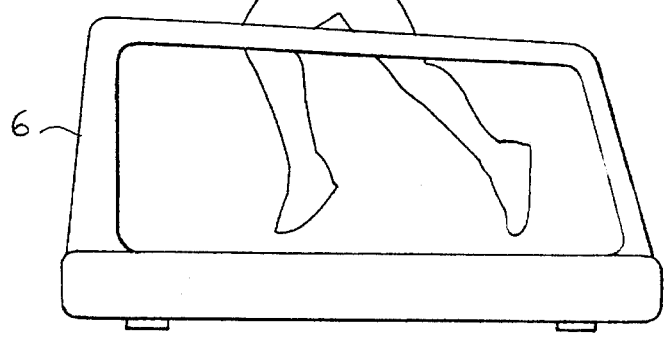
FIG. 3 is a view of the dashboard of the control unit of a programmable cycle ergometer provided with pulse receiving and processing means for carrying out the invention.

In FIG. 3, an enlarged view of the dashboard 9 of the control unit 8 of a programmable cycle ergometer according to FIG. 1 is shown. As stated above, the control unit 8 may be provided with pulse receiving and processing means for carrying out the invention as such, or these may be provided optionally as a separate unit, connecting to the control unit 8 by means of any standard computer interface, such as a serial RS 232- interface. In the embodiment shown in FIG. 2, an integrated version of the pulse receiving and processing means is assumed. On the dashboard, fairly conventional speed and clock display means 10 and 11 can be recognized. The speed meter 10 helps the person using the cycle ergometer to keep a constant pace during the whole performance, which is essential for the results from each test occasion to be comparable.

The clock 11 shows the time elapsed from the beginning of the test. The chosen exercise profile is shown on display 12 as a track of illuminating components, such as LEDs. The load coefficient of the profile, which can be separately chosen, e.g. between values 0–9, is shown on display 13. In the case of a treadmill, the variation in excercise performance is achieved e.g. by setting and/or varying the running speed of the belt in a predetermined pattern according to the performance level of the user.

For clarity, the programming keyboard is not shown here. Display 14 is the pulse display. One can chose between a current pulse display mode (by pushing button C), which shows the user's pulse rate at the instant moment, and a mean pulse value display mode (by pushing button M), which show, on the basis of data accumulated so far, the calculated mean pulse value. Depending on the mode of operation, the control unit 8 may give an audible or visible signal, when the predetermined performance time is out (performance by means of a constant exercise program), or when the predetermined mean value pulse rate is achieved (constant heart performance by means of a variable exercise program). Also, the relevant mean value pulse may then be frozen in the pulse display for an appropriate time in order for the test person or his coach to read and memorize the result.

Processing the received pulse signals may include storing the measured pulse values cumulatively in a memory of the receiver means and processing them with the aid of a micro computer included in the receiving means. It is also possible to use a mathemathical algorithm that continuously calculates the mean value of the measured pulse rates accumulated, whereby extensive storage of the pulse rates is not neccessary. It is also ordinary design considerations of one skilled in the art whether the mean value processing means is to be included in a (separate) receiver means or in the control unit of the excercise device.

It is obvious to one skilled in the art that the different embodiments of the invention are not restricted to the above-described examples, but they may vary within the scope of the following claims.

I claim:

1. A method for measuring a heartbeat pulse of a person using an exercise device for physical performance, the method comprising the steps of:

programming the exercise device to provide an exercise program for a user of the device to perform;

detecting a heartbeat pulse during the performance of the exercise program and transmitting heartbeat pulse signals corresponding to said heartbeat pulse detected with a transmitter attached to the user;

receiving the transmitted heartbeat pulse signals with a receiver connected to the exercise device;

processing the received heartbeat pulse signals; and calculating a mean heartbeat pulse value from all of the heartbeat pulse signals received during the performance of the program and displaying the calculated mean heartbeat pulse value to the user at the end of the program.

2. The method of claim 1, comprising transmitting the heartbeat pulse signals during the performance of the exercise program from a telemetric wireless transmitter attached to the user and receiving the transmitted heartbeat pulse signals with a telemetric wireless receiver connected to the exercise device.

3. An apparatus for measuring a mean heartbeat pulse of a person during physical performance of an exercise program on an exercise device, comprising an exercise device, means for programming the exercise device to provide an exercise program for a user of the device to perform, heartbeat pulse detector means attachable to the user for generating heartbeat pulse signals indicative of the heartbeat pulse detected during the performance of the exercise program, heartbeat pulse signal transmitter means attachable to the user for transmitting said heartbeat pulse signals, receiver means connected to said exercise device for receiving said heartbeat pulse signals transmitted by said transmitter means, processing means for calculating at the end of the program a mean heartbeat pulse value of the person using the exercise device from all of the heartbeat pulse signals received during the performance of the program, and display means for displaying said calculated mean heartbeat pulse value to the person using said exercise device at the end of the program.

4. The apparatus of claim 3, including a control means for controlling operation of said exercise device and wherein the receiver means is connected to the control means.

5. The apparatus of claim 3 or 4, wherein the exercise device is a cycle ergometer.

6. The apparatus of claim 3 or 4, wherein the exercise device is a treadmill.

7. The apparatus of claim 3 or 4, wherein the transmitter means comprises a telemetric wireless transmitter attachable to the person using the device, and the receiver means comprises a telemetric wireless receiver connected to the exercise device.

\* \* \* \* \*